(12) United States Patent
Valonen et al.

(10) Patent No.: US 11,261,416 B2
(45) Date of Patent: Mar. 1, 2022

(54) FIXED-BED BIOREACTOR WITH CONSTANT-FLOW PUMP / TUBING SYSTEM

(71) Applicant: Trizell Ltd., Chinnor (GB)

(72) Inventors: Piia Kristiina Valonen, Kuopio (FI); Hanna P. Lesch, Kuopio (FI); Eva Kristiina Rasanen, Hiltulanlahti (FI); Tarja Hannele Tuunanen, Copy (FI); Minna Kristiina Karhinen, Kuopio (FI); Seppo Yla-Herttuala, Kuopio (FI)

(73) Assignee: Trizell Ltd., West Drayton (GB)

( * ) Notice: Subject to any disclaimer, the term of this patent is extended or adjusted under 35 U.S.C. 154(b) by 94 days.

(21) Appl. No.: 15/579,208

(22) PCT Filed: Apr. 3, 2017

(86) PCT No.: PCT/US2017/025681
§ 371 (c)(1),
(2) Date: Dec. 3, 2017

(87) PCT Pub. No.: WO2017/180341
PCT Pub. Date: Oct. 19, 2017

(65) Prior Publication Data
US 2019/0031998 A1  Jan. 31, 2019

Related U.S. Application Data

(60) Provisional application No. 62/322,651, filed on Apr. 14, 2016.

(51) Int. Cl.
| C12M 1/00 | (2006.01) |
| C12M 1/02 | (2006.01) |
| C12P 21/02 | (2006.01) |
| C12M 1/12 | (2006.01) |
| C12N 15/86 | (2006.01) |
| C12M 1/34 | (2006.01) |
| C07K 14/005 | (2006.01) |

(52) U.S. Cl.
CPC ........... *C12M 29/18* (2013.01); *C07K 14/005* (2013.01); *C12M 1/02* (2013.01); *C12M 25/18* (2013.01); *C12M 29/10* (2013.01); *C12M 41/26* (2013.01); *C12M 41/46* (2013.01); *C12N 15/86* (2013.01); *C12P 21/02* (2013.01); *C12N 2740/15051* (2013.01)

(58) Field of Classification Search
None
See application file for complete search history.

(56) References Cited

U.S. PATENT DOCUMENTS

| 5,622,857 A | 4/1997 | Goffe | |
| 2002/0177215 A1* | 11/2002 | Zhang | C12N 15/86 |
| | | | 435/235.1 |
| 2005/0201983 A1 | 9/2005 | Yla-Herttuala et al. | |
| 2011/0189764 A1* | 8/2011 | Starbard | C12M 1/00 |
| | | | 435/289.1 |
| 2014/0255994 A1* | 9/2014 | Konstantinov | C07K 1/36 |
| | | | 435/69.6 |
| 2019/0218495 A1 | 7/2019 | Valonen et al. | |
| 2020/0165557 A1 | 5/2020 | Lesch et al. | |

FOREIGN PATENT DOCUMENTS

| EP | 0295567 A1 | 12/1988 |
| WO | WO-2005/095578 A1 | 10/2005 |
| WO | WO-2014/130864 A2 | 8/2014 |
| WO | WO2016048556 * | 3/2016 |
| WO | WO-2017/180341 A2 | 10/2017 |
| WO | WO-2018/007873 A1 | 1/2018 |

OTHER PUBLICATIONS

Ansorge, S. et al., Development of a scalable process for high-yield lentiviral vector production by transient transfection of HEK293 suspension cultures, Journal of Gene Medicine, 11(10): 868-876 (2009).
Chahal, P. S, et al., Production of adeno-associated virus (AAV) serotypes by transient transfection of HEK293 cell suspension cultures for gene delivery, Journal of Virological Methods 196:163-173 (2014).
Chiorini, J. A. et al., Cloning and characterization of adeno-associated virus type 5, Journal of Virology, 73(2):1309-1319 (1999).
Coleman, J. E. et al., Efficient large-scale production and concentration of HIV-I-based lentiviral vectors for use in vivo, Physiol Genomics, 12(3):221-228 (2003).
Cortin, V., et al., A. High-titer adenovirns vector production in 293S cell perfusion culture, Biotechnol Prog., 20(3):858-63 (2004).
Dormond, E., et al., From the first to the third generation adenoviral vector: what parameters are governing the production yield?, Biotechnol Adv., 27(2):133-44 (2009).
Ferreira ,T. B., Effect ofre feed strategies and non-ammoniagenic medium on adenovirns production at high cell densities, J. Biotechnol., 119(3):272-80 (2005).
Follenzi, A. and Naldini, L., Generation of HIV-I derived lentiviral vectors, Methods Enzymol., 346:454-465 (2002).
Geraerts, M., et al., Upscaling of lentiviral vector production by tangential flow filtration., J. Gene Med., 7:1299-1310 (2005).

(Continued)

*Primary Examiner* — Christian L Fronda

(74) *Attorney, Agent, or Firm* — Choate, Hall & Stewart LLP; Rolando Medina

(57) ABSTRACT

We have modified a commercially-available adherent cell culture bioreactor in several ways to increase productivity of cultured cells, while decreasing contamination risk. We found that modifying a commercially-available adherent cell culture bioreactor to provide for slower cell culture medium flow unexpectedly and dramatically increases the productivity of the cultured adherent cells. We also developed a new sampling manifold configuration and new way of taking samples, to reduce contamination risk.

37 Claims, 3 Drawing Sheets

(56) References Cited

OTHER PUBLICATIONS iCELLis® 500 Bioreactor Revision E Controller, Pall Life Sciences, Instructions for Use, Handbook, 151 pages.
iCELLis® 500 Revision E Controller Instructions for Use, Handbook, Pall Life Sciences, 153 pages.
International Search Report for PCT/IB2017/001205, 6 pages (dated Nov. 29, 2017).
International Search Report for PCT/US2017/025681, 3 pages (dated Oct. 2, 2017).
Iyer P, et al., Comparison of manufacturing techniques for adenovirus production., Cytotechnology., 30:169-72 (1999).
Kamen A. and Henry, O., Development and optimization of an adenovirus production process., J Gene Med., 6 Suppl 1:S184-S192 (2004).
Karolewski, B. A. et al., Comparison of transfection conditions for a lentivirus vector produced in large volumes, Hum. Gene Ther., 14(14):1287-1296 (2003).
Koldej, R. et al., Optimisation of a multipartite human immunodeficiency virus based vector system; control of virus infectivity and large-scale production, J. Gene Med., 7:1390-1399 (2005).
Kudora, H. et al., Simplified lentivirus vector production in protein-free media using polyethylenimine-mediated transfection, J. Virol. Methods, 157(2):113-121 (2009).
Lennaertz, A. et al., Viral vector production in the integrityi:ID iCELLis@ single-use fixed-bed bioreactor, from bench-scale to industrial scale, BMC Proceedings, 7(Suppl 6):59-60 (2013).
Lesch, H. P. et al., Process Development of Adenoviral Vector Production in Fixed Bed Bioreactor: From Bench to Commercial Seale, Human Gene Therapy, 26(8): 560-571 (2015).
Liu, H. et al., A high-yield and scaleable adenovirus vector production process based on high density perit1sion culture of HEK 293 cells as suspended aggregates, J. Biosci. Bioeng., 107(5):524-9 (2009).
Meuwly, F. et al., Packed-bed bioreactors for mammalian cell culture: bioprocess and biomedical applications, Biotechnol Adv., 25(1):45-56 (2007).
Naldini, L. et al., Efficient transfer, integration, and sustained long-term expression of the transgene in adult rat brains injected with a lentiviral vector, Proc. Natl. Acad. Sci., 93:11382-11388 (1996).
Petiot, E. et al., Influence of HEK293 metabolism on the production of viral vectors and vaccine, Vaccine, 33(44):5974-81 (2015).
Rajendran, R. et al., Assessment of packed bed bioreactor systems in the production of viral vaccines, AMB Express, 4:25 (2014).
Reiser, J., Production and concentration of pseudotyped HIV-I-based gene transfer vectors, Gene Ther., 7:910-913 (2000).
Rodrigues, A. F. et al., Retroviral vector production under serum deprivation: The role of lipids, Biotechnol Bioeng., 104(6):1171-81 (2009).
Segura, M. M. et al., Production oflentiviral vectors by large-scale transient transfection of suspension cultures and affinity chromatography purification, Biotechnol. Bioeng., 98(4):789-799 (2007).
Seifert, G. K. E. and Matteau, P. P., An Automatic Aseptic Bioreactor Sampling System, Biotechnology and Bioengineering, 32:923-926 (1988).
Sena-Esteves, M. et al., Optimized large-scale production of high titer lentivirus vector pseudotypes., J. Virol. Methods, 122(2):131-139 (2004).
Slepushkin,V. et al., Large-scale Purification of a Lentiviral Vector by Size Exclusion Chromatography or Mustang Q Ion Exchange Capsule, BioProcessing Journal 2:89-95 (2003).
Tiscornia, G. et al., Production and purification of lentiviral vectors, Nat. Protoc., 1:241-245. (2006).
Vellinga, J. et al., Challenges in Manufacturing Adenoviral Vectros for Global Vaccine Product Deployment, Human Gene Therapy, 25:318-327 (2014).
Wang, X. et al., Large-scale Clinical-grade Retroviral Vector Production in a Fixed-Bed Bioreactor., J. Immunother., 38(3):127-135 (2015).
Written Opinion for PCT/IB2017/001205, 7 pages (dated Nov. 29, 2017).
Written Opinion for PCT/US2017/025681, 13 pages (dated Oct. 2, 2017).
Wu, S. C. et al., Production ofretrovirus and adenovirus vectors for gene therapy: a comparative study using microcanier and stationary cell culture, Biotechnol Prog., 18(3):617-22 (2002).
Drouin, H., Increasing the Performance of Mammalian Perfusion Culture System, A thesis submitted in partial fulfillment of the requirement for the degree of doctor of philosophy, The University of British Columbia, 170 pages (2010).

* cited by examiner

FIXED-BED BIOREACTOR WITH CONSTANT-FLOW PUMP / TUBING SYSTEM

RELATED APPLICATIONS

This application is a National Stage of Patent Cooperation Treaty application Serial No. PCT/US2017/025681 filed 03 Apr. 2017, which asserts priority to United States provisional patent filing Serial No. 62/322,651, filed 14 Apr. 2016, the contents of which are here incorporated by reference.

GOVERNMENT INTEREST

None.

BACKGROUND

We have improved commercial-scale adherent cell culture by developing an improved bioreactor which provides a ~50% increase in productivity viz prior art bioreactors, while also eliminating a source of contamination.

Commercially-available adherent cell culture bioreactors include, for example, the laboratory-scale iCELLis™ Nano (commercially available from Pall Corporation, Cambridge Ma.) and the commercial scale iCELLis™ 500 bioreactor, which provides a volume of up to 74 liters of cell culture medium and a cell culture substrate of medical grade polyester microfibers which provide up to 500m$^2$ growth area available to the cells. We improved the function of such commercial-scale bioreactors by first, defining the process steps in a small scale and then scaling these up into a large scale. Pall Life Science, the manufacturer of the iCELLis™ brand of bioreactors, was recommending re-circulation or perfusion as a feeding strategy. The feeding strategy in small (Nano™) scale was tested by re-circulation, and later optimized by perfusion.

Perfusion is a process step where cells in a bioreactor are continuously feed with a fresh medium at the same time removing equal amount of spend medium, which enables the cell growth in high cell density (Vellinga et al. 2014). The perfusion rate can vary depending on the type of cell line used, the polypeptide product produced by those cells, the specific cell culture medium employed and the cell growth system used. An important aspect in the removal of the spent medium is also to remove the (possible toxic) metabolic side products from the cell culture. These side products may have a negative effect on cell viability, and further may impair the productivity of producer or host cells.

Options for perfusion include batch perfusion and fed-batch perfusion (where feeding of fresh medium is performed but no removal of spend medium is performed). The fed-batch type approach is also a re-circulation strategy, where the cell culture medium volume is only enlarged by external medium container and medium is re-circulated from a media reservoir or container to the bioreactor and back again, wherein no actual removal of spend or used medium is done.

The manufacturer of the iCELLis™ line of bioreactors (Pall Life Technologies) markets the iCELLis™ 500 as suitable for perfusion feeding. We made a very surprising finding during our first experiment with iCELLis™ 500: as provided by the manufacturer, the equipment is not in fact capable of perfusion, if using the standard iCELLis™ 500 tubing and pump system set at the slowest pump output rate available.

We deconstructed the commercially-available apparatus and found out the reasons for failure. The commercially-available apparatus is manufactured with the feed-out tube of larger interior diameter than the feed-in tube. This configuration is intedned to prevent unwanted overflow of the liquid media by ensuring that in-flow cannot be greater than out-flow. We surprisingly found that this configuration adversely impacts pump efficiency and the productivity of the cultured cells Rather, we found the feed-out tube is best of equal or smaller interior diameter than the feed-in tube. We found that the commercially-provided ("stock") medium feed-out tube was of too large interior diameter, providing a too-large interior volume space for the media flow rate. This large interior tube volume permitted formation of undesirable air pockets and bubbles in the tubing.

In addition, the stock feed-out tube was integrated into a too-weak pump system which could not provide an adequate media flow out from the bioreactor. This may be because formation of air bubbles in turn appears to affect the correct out feed-out pump capacity. The feed-out pump works by creating negative pressure in the feed-out tube, pulling media into the feed-out tube. Unlike liquid media, however, air bubbles expand in this negative-pressure environment, absorbing much of the negative pressure energy, thus frustrating pump work.

BRIEF DESCRIPTION

We resolved the failures inherent in the commercially-available apparatus by retrofitting the bioreactor with a bigger peristaltic pump able to provide the proper (lower) rate of fluid output, and replacing the feed-out tubing with replacement tubing having a smaller inside diameter, thus preventing formation of undesirable air bubbles in the feed-out tubing.

Another suggestion we have made for the manufacturer is to make bioreactors with smaller tubing diameter to improve the medium flow inside tubing.

We also have designed and tested a new sampling manifold configuration which eliminates the risk that a compromised aseptic filter will contaminate an entire manufacturing batch.

DETAILED DESCRIPTION

Figure 1:
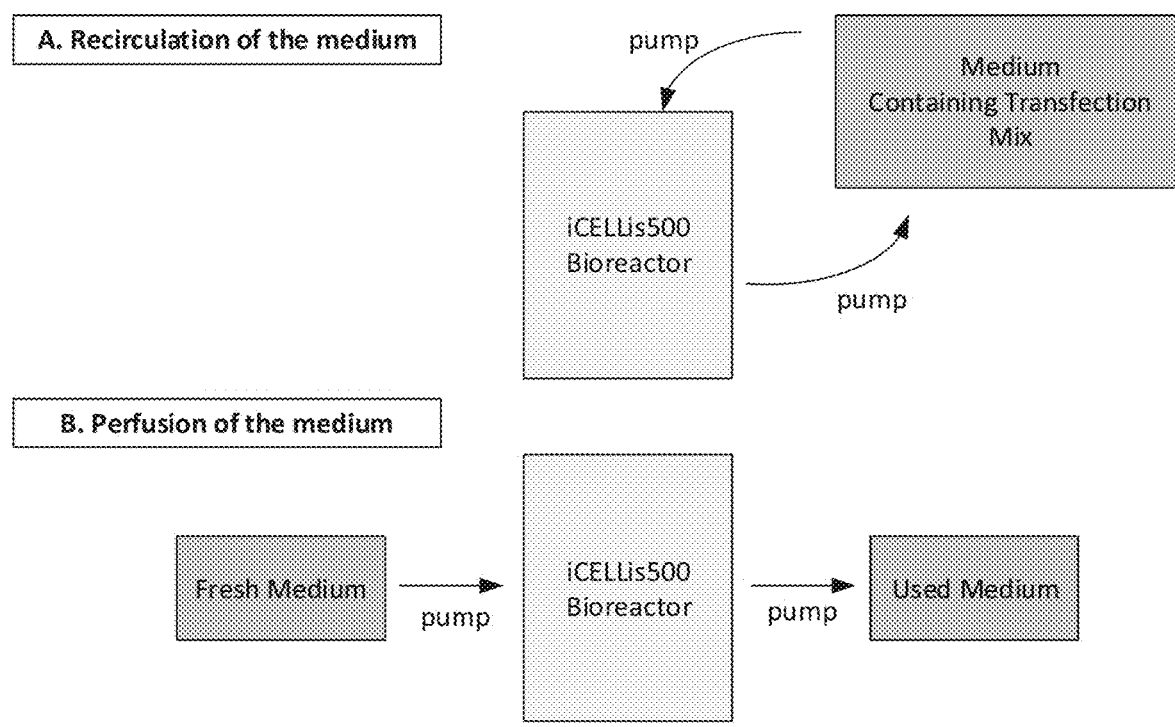
FIG. 1 schematically illustrates two different perfusion methods

We have implemented a way to improve medium feed in and feed out strategy in large capacity adherent cell culture bioreactors such as, for example, the iCELLis™ 500 bioreactor. Commercially-available large scale bioreactors are designed to recirculate media at high velocity; we found that perfusing media at a low velocity unexpectedly increases producer cell output Our approach is the only suitable way to achieve acceptably slow and constant cell culture medium flow into and out of the bioreactor vessel. Constant medium flow supports high viral productivity for infected, transfected or transduced producer cells, while avoiding excessive medium usage.

Adherent cell culture bioreactor vessels provide a substrate on which cultured cells can adhere and grow. That substrate is housed in a container which contains liquid cell culture media.

Commercially-available large capacity adherent cell culture bioreactors are provided with "Feed In" and "Feed Out" pumps. These pumps respectively pump cell culture media into and out of the container which contains the substrate, thus providing the cultured cells with fresh culture media, and removing spent media and its appurtenant culture waste products.

Example 1—Intermittent Pumping

Pumps can be programmed to run constantly. Run constantly at minimum speed, the prior art iCELLis™ 500 Feed In and Feed Out pumps produce at least about 42.3 L of medium flow per day (running at the slowest rate possible, 24 rpm). The capacity of the bioreactor vessel being about 25 liters, the medium in the reactor is completely exchanged almost twice a day.

We used a commercially-available large capacity adherent cell culture bioreactor vessel to culture transfected "producer" cells which express viral polypeptides and produce viral particles. We found that these producer cells are most productive when the cell culture medium is perfused at a rate slower than the slowest pump output volume available in commercially-available apparatus. To be able to get a properly low medium perfusion rate for our purposes, we programmed the pumps to run for certain time interval, followed by an interval where the pumps did not pump at all.

Because of this need to vary pump output, we have seen in practice that the stock iCELLis™ 500 bioreactor Feed Out pump provided by the manufacturer is not capable of removing medium out from the bioreactor vessel in a well controlled manner. We thus becan to test the viability of lower-output pumps able to provide an adequately low output flow.

Example 2—Constant Low-Velocity Pumping

We then investigated whether the variable media flow used in the prior art might impact cell culture in some way. To do this, we replaced the prior art Feed In pump provided with the iCELLis™ 500 bioreactor with a replacement pump which was able to provide a lower output volume, about 16.7 L/day. For a 25 liter capacity bioreactor vessel, this means the media in the vessel would be exchanged once every 3½ to 4½ days, rather than the nearly twice a day typical in the prior art. This reduces the flow across e.g., a 100 m$^2$ substrate surface area from at least 42.3 L per 100 m$^2$ per day to 16.7 L per 100 m$^2$ per day. This lower Feed In pump rate enabled us to for the first time to run the Feed In pump constantly, without periodic stoppages.

During these runs it was observed that the Feed Out pump provided by the manufacturer was not able to perform the removal of the media from the bioreactor vessel throughout the process as planned. We therefore similarly replaced the prior art Feed Out pump provided by the manufacturer with a lower-output pump.

We performed a commercial-scale manufacturing run, using recombinant adherent producer cells to produce a recombinant adenovirus bearing a transgene (useful for e.g., gene therapy), using in the adherent cell culture process a combination of the stock iCELLis™ 500 Feed In pump and our own lower-output Feed Out pump. Our method is generally advantageous in producing vector with any kind of transgene (including therapeutic transgenes and marker transgenes such as green fluorescent protein), or any other genetic element or nucleotide sequence (e.g., viral vector containing RNA transgene, shRNA, IngRNA, eRNA etc.).

We also performed three commercial-scale manufacturing runs, wherein we used our own lower-output Feed Out pump and also replaced the stock iCELLis™ 500 high-output Feed In pump also with a lower-output pump. We received significantly higher adenoviral production in the adherent producer cells in each of these three runs. In these three runs, the productivity of viral particles per cell had increased 49.4% as compared to productivity using the prior art higher-output pumps.

When we changed the process to work with lower-output pumps, our viral productivity per cell surprisingly increased 49.4%. Without intending for the legal coverage of our patent to be bound by any scientific causal theory, this improvement may be due to feeding the bioreactor vessel constantly with fresh medium, thereby keeping stable the level of nutrients in the media in contact with the cultured cells. For example, we have found that adherent cells are most productive when the media flow is substantially constant and slow enough to maintain in the cell culture medium a level of lactate of not more than about 1.6 grams lactate/ liter of culture medium. Similarly, we have found that certain adherent producer cells are most productive when the concentration of glucose in the culture media is maintained at between about 0.5 and about 1.0 grams of glucose per liter of media. Other adherent producer cells are most productive with a glucose concentration which is higher (e.g., at least about 2.9 grams per liter) but nonetheless maintained at a relatively constant concentration due to low-velocity but substantially constant media flow. Alternatively, this may be due to the slow but constant flushing away of unwanted cellular waste products from the cell surface. Alternatively, this could be due to avoiding the physical shear stress placed on the cultured cells when using the higher-velocity media flow required by prior art hardware. Alternatively, this increase could be due to slower media flow enabling each producer cell a longer time to produce virus-like particles. Whatever the cause (or causes), we found that a slower, constant medium flow surprisingly and significantly increased adherent producer cell productivity.

This increase is particularly surprising in light of the fact that suspension cell culture (e.g., the CultiBag RM™ suspension cell culture bag, commercially available from Sartorius Corp., Cambridge Mass.) provides more-or-less constant media flow across the cell surface, yet suspension cell culture can be as less productive than adherent cell culture.

Lower-output pumps may also be successfully used for inoculation of the host cells into the adherent bioreactor vessel, for drawing samples of the cell culture media during cell growth, and for harvesting e.g., culture media at the end of the cell growth. We have surprisingly found that using a lower-output pump to perform these functions counterintuitively makes each of those processes faster than with the prior art high-output pumps.

One may replicate our system by simply obtaining a commercially-available large-scale adherent cell culture bioreactor vessel, disconnecting the Feed In and Feed Out tubing from the pumps provided with that bioreactor, and connecting that tubing to external pumps. With external pumps, however, the operator may lose the ability to control the external pumps through the computer which controls the bioreactor (and its integral pumps). For example, commercially available large scale adherent bioreactors typically include a sensor which measures the level of liquid cell culture medium in the bioreactor vessel, to monitor whether the cell culture substrate is adequately submerged in medium External pumps may not be automatically controlled by the feedback control loops that are automatically activated by the liquid cell culture medium level sensed in the bioreactor vessel. Similarly, commercially available large scale adherent bioreactors typically include a recording device which records the running speeds of the pumps. Using external pumps, the output may not be recorded automatically to the computer One may overcome these disadvantages by calibrating the external pumps before use and manually monitoring the culture medium flow in and out from the bioreactor vessel regularly, and by recording all steps manually to the batch manufacturing records. Alternatively, one can connect the new pumps to the bioreactor control computer, so that the low output pumps can be controlled and monitored similarly and simultaneously, as for the bioreactor itself.

The pump(s) can be controlled by software or through external calibration, or by controlling by nominal motor speed (RPMs), or using a balance or weight-control led system. Alternatively, the pump(s) may be controlled manually, or have an automatic speed control or any other suitable way to control the pump The precise control method is not critical, as long as the pump is able to provide the consistent low-flow output we have surprisingly found is favorable to increased adherent cell production.

Our lower flow rate is effective for larger-area adherent cell cassettes (e.g., a 500 m$^2$ cassette). Lower flow rate may also be effectively used with smaller-area substrate cassettes, such as 66 m$^2$ fiber cassettes.

Our system can be used to culture adherent producer cells which express viral polypeptide and thus produce recombinant virus or virus-like particles (we use the term "virus" in our appended legal claims to encompass both viruses and virus-like particles)

Example 3—Unidirectional Sampling Manifold

A bioreactor sampling manifold is used for taking liquid samples of the cell culture medium from the bioreactor vessel to e.g., check pH, or to measure glucose, metabolites and cell waste products (e.g., lactate) or other substances in the medium.

We unexpectedly found that the stock sampling manifold offered as part of the commercially-available iCELLis™ is vulnerable to contamination. We have successfully designed a new sampling manifold for the bioreactor for removing the need of pumping medium in and out from the bioreactor vessel into a sampling bottle This way we minimize the risk of contamination due to a sampling.

Figure 2:
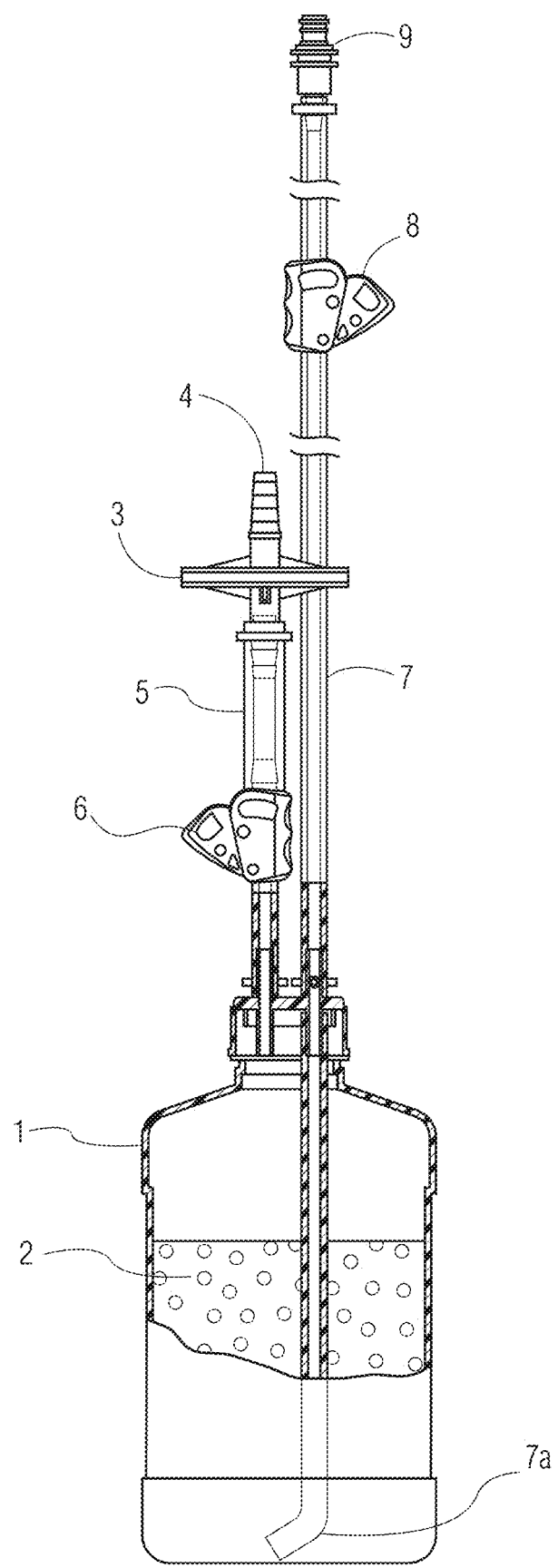
FIG. 2 shows a way to connect a bioreactor vessel to a sampling manifold

A schematic drawing of an adherent culture bioreactor is shown in FIG. 2. The bioreactor is comprised of a vessel [1] which contains a cell culture substrate [2] to which cells adhere when cultured in adherent mode. The vessel [1] is filled with liquid cell culture medium which irrigates the cell culture substrate [2]. The vessel [1] has a vent which includes an air filter [3] having an exit vent [4]. The exit vent [4] is able to vent excess gas out of the bioreactor vessel and the filter [3] filters the gas flowing through the filter to prevent particulate contaminants (e.g., viral particles, fungal spores) from exiting or entering the bioreactor vessel. The filter [3] is preferably detachably connected to the vessel [1] via a vent tube [5], Alternatively, the filter may be integrated into the body of the vessel [1], albeit this risks enabling liquid cell culture media to splash onto the filter and occlude it. Preferably, the vent tube has a clamp [6] which enables a technician to close the vent tube [5] as and when desired.

The vessel [1] also has a sampling tube [7] with an input end [7a] which passes into the liquid cell culture medium and thus is able to intake liquid medium. Preferably, the sampling tube [7] also has a clamp [8] which enables a technician to close the sampling tube [7] as when desired The sampling tube [7] has a connection [9] enabling it to be connected to a sampling device. The sampling device may be a detachable sampling bag or bottle. We prefer, however, the sampling device comprise a sampling manifold [FIG. 3] able to connect to a pair of detachable sampling bags or bottles.

Figure 3:
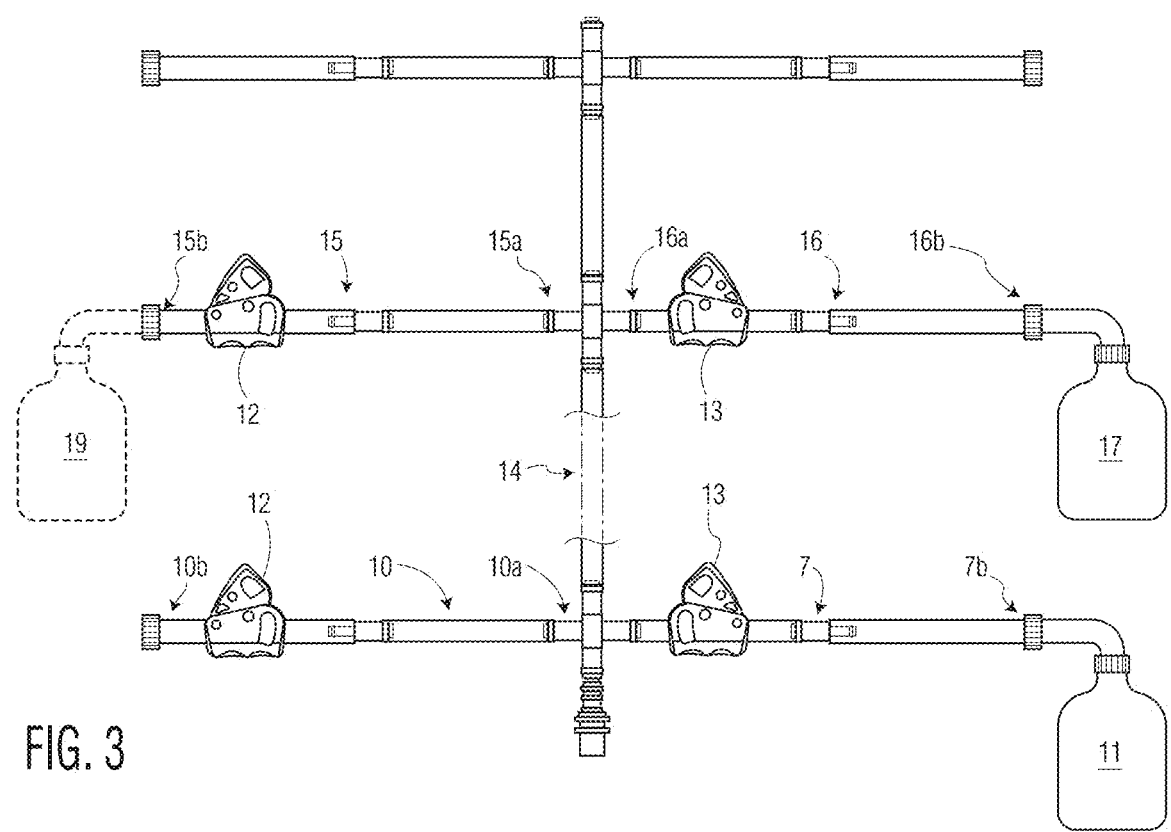
FIG. 3 shows a version of our improved sampling manifold.

The sampling manifold [FIG. 3] is connected [9] to the sampling tube [7], The sampling manifold comprises a waste tube [10] having an input end [10a] and an output end [10b], and the sampling tube [7] output end [7b] able to connect to a removable sampling container [11]. The sampling container [11] may be, for example, a bag or a bottle.

The prior art commercially-available sampling manifold is based on the idea that first approximately 200 ml of cell culture media is merely a rinse; it is pumped through the manifold to rinse the interior of the manifold That rinse media passes out of the manifold through an exit opening into a temporary storage bottle. Additional cell culture media is then pumped through the manifold, and a sample is collected. After the sample is taken, the approximately 200 ml of cell culture rinse media which was initially collected in the temporary storage bottle is pumped from the bottle back into the manifold and back into the bioreactor vessel [1], so that as little as media as possible remains inside the sampling manifold The temporary storage bottle and the tubing can be emptied because the prior art configuration provides an aseptic filter in the sampling bottle, which filter permits ambient air to exit and enter the bottle (when liquid is pumped into and out of the bottle, respectively), the filter filtering airborne contaminants in the ambient air and thus preventing contamination of the cell culture medium.

If the integrity of the filter is compromised, however, this can pose a major contamination risk which is difficult to detect until an entire manufacturing batch has been contaminated Using the commercially-available prior art configuration, we have in fact incurred a contamination of a commercial-scale manufacturing batch In evaluating the failure, it was observed that the aseptic air filter in a sampling bottle was broken, but it remained unclear how it had broken.

We thus designed a new sampling manifold using a different sampling technique. We have tested it successfully in at least four commercial-scale manufacturing batches, and have encountered no problems.

With our sampling manifold we eliminate the need to pump cell culture media liquid out from the bioreactor vessel and then back again Rather, with our sampling manifold, when liquid is taken from the bioreactor vessel, it is never pumped back in again. This reduces the risk of contamination significantly.

Our sampling manifold is described in FIG. 3. We prefer to make our sampling manifold from commercially-available C-flex tubing, Masterflex™ tubing, clamps, and commercially-available polymer tube connectors. The tubing can be non-sterile or sterilized by e.g., temperature- or moisture-based techniques such as autoclaving, or gamma-irradiated or gas-based sterilization such as ethylene. The tubing can be ready-made, or custom-made by the user. We merely prefer it to be compatible with commercially-available sterile connections, thus able to be branched with any type connections, and suitable for sealing and welding.

Our sampling manifold can be connected to a bioreactor such as the iCELLis™ 500 bioreactor through MPC-connector. When used with an iCELLis bioreactor, our sampling manifold can entirely replace the sampling manifold offered by Pall Life Sciences as part of their commercially available Starter Kit, which is marketed together with the iCELLis™ 500 bioreactor.

In our sampling manifold, we use a pair of tubes to take one sample. One tube is used to rinse the manifold interior, the other tube is used after rinsing to take the sample. For example, one can use tube [15] to rinse the manifold and then use tube [7] to take a sample.

To begin, a single-use sampling bag or bottle [11, 17, 19] is aseptically attached (we prefer through wielding) to the sampling tube [7], One may (and we prefer) to also attach a sampling bag [19] to the first (rinse) line of the pair [15]. Alternatively, the first line may drain into a waste bottle etc.

To use our sampling manifold, liquid cell culture media is pumped from the bioreactor vessel [1] or an accompanying media reservoir through the manifold to rinse the interior. This is for rinsing the manifold and getting fresh medium/liquid from the vessel [1] into the manifold. This rinse media is removed from the manifold via a rinse tube [15] into a rinse media container [19]. Eherinse tube [15] is then sealed or closed. This may be done with a tubing clamp [12] (as illustrated). Alternatively, the tubing may be sealed with an end cap [on 15b], or welded closed [at 15b], etc.: the manner of sealing is not particularly important here. The rinse tube [15] thereafter remains sealed off for the remainder of the manufacturing run. In the appended legal claims, we refer to sealing off for the remainder of the manufacturing run as "permanent" sealing because in the context of a given manufacturing run, it is effectively permanent (i.e., lasting to the end).

The sampling tube exit end [7b], going to the sample container [11], is then opened [13]. Fresh medium/liquid is pumped from the bioreactor vessel [1] (e.g., from the part of the bioreactor which houses the adherent cell culture substrate) into the sampling tube [7], and then out of it [7b] into the sampling container [11]. While we illustrate one sample container ([11]), one could alternatively use several sample containers and take several physically-separate samples. The sampling tube [7] is then closed [13]. The sampling container [11] may then be sealed and removed from the sampling tube output [7b]. After taking the sample, the pair of manifold branches [15, 7] remain sealed off for the remaining duration of the manufacturing run. We prefer both tubes be drained to remove residual media, to reduce risk of contamination.

Sampling bags [11] provide a sampling port used for aseptically drawing liquid out of the sampling bag to assay. Several samples can thus be taken from one bag aseptically.

To enable sequential sampling at different times, we prefer to provide several pair of sampling tubes. With this, a second (or subsequent) sampling may be performed in a similar fashion as the first one, using a different pair of manifold tubes and a second sampling bag attached to the second tube of that second pair of tubes. For example, to take a second sample, one may use line [10] as the rinse tube and line [16] as the sampling tube, with the sample being taken in container [17]). Media/liquid that has remained in the manifold since the first sampling is discarded by pumping it out of the manifold [10b], preferably into a rinse or waste receptacle or container until fresh media/liquid from the bioreactor substrate has filled the manifold. This second rinse tube [10] is then sealed or closed. This may be done with a tubing clamp [12] (as illustrated). Alternatively, the tubing may be sealed with an end cap, or welded closed, etc.: the manner of sealing is not particularly important here. The second rinse tube [10] thereafter remains sealed off for the remainder of the manufacturing run.

The second sampling tube [16] is then opened [13]. Fresh medium/liquid is pumped from the bioreactor vessel [1] (e.g., from the part of the bioreactor which houses the adherent cell culture substrate) into the second sampling tube [16] and then out of it [16b] into a second sampling containers) [17]. The sampling tube of the second pair [16] is then closed [13]. The sampling container(s) [17] may then be sealed and removed. After taking the sample, the pair of manifold branches [10, 16] remain sealed off for the remaining duration of the manufacturing run.

This configuration may be repeated as desired, providing as many pair of rinse and sampel tubes as desired to enable as many different sampling times as desired.

With our sampling port, a disadvantage at the moment is the need to construct the manifold (rather than be able to purchase it commercially). Another disadvantage could be the use of several sampling bags for each manufacturing batch. These disadvantages, however, are more than off-set by the reduced possibility of contaminating a manufacturing batch, which in commercial-scale manufacturing poses a significant financial risk.

We claim:

1. An adherent cell culture bioreactor comprising a substrate for adherent cell growth, a feed-in pump and a feed-out pump, wherein the feed-in pump and the feed-out pump are configured to provide a constant-rate output of cell culture media of less than about 50 mL of media per 1,800 cells per day.

2. The adherent cell culture bioreactor of claim 1, wherein the feed-in pump and the feed-out pump are able to provide a minimum constant-rate output of not more than about 16.7 mL of media per 1,800 cells per day.

3. The adherent cell culture bioreactor of claim 1, wherein the substrate comprises at least about 60 $m^2$ of surface area for adherent cell culture.

4. The adherent cell culture bioreactor of claim 3, wherein the substrate comprises at least about 400 $m^2$ of surface area for adherent cell culture.

5. The adherent cell culture bioreactor of claim 1, wherein the bioreactor provides a volume of at least about 20 liters of cell culture media.

6. A method for culturing adherent cells on a substrate comprising:
   a. obtaining the bioreactor of claim 1, and then
   b. adding to the bioreactor cell culture media and cells, and then
   c. culturing the cells in adherent mode on the substrate, while circulating the cell culture media about the cells at a rate of less than about 50 mL of media per 1,800 cells per day.

7. The method of claim 6, wherein the substrate comprises at least about 400 $m^2$ of surface area for adherent cell culture.

8. The method of claim 6, wherein the bioreactor provides a volume of at least about 20 liters of cell culture media.

9. An adherent-cell culture bioreactor comprising a substrate for adherent cell growth, a feed-in pump and a feed-out pump, wherein the feed-in pump and the feed-out pump are configured to be able to provide a constant-rate output of cell culture media at a pump output volume sufficient to maintain in said cell culture medium a parameter selected from the group consisting of: concentration of lactate in said medium of not more than about 1.58 grams/ liter; and concentration of glucose in said medium of between about 0.5 and 1.0 grams/liter.

10. The adherent cell culture bioreactor of claim 9, wherein the bioreactor provides a volume of at least about 20 liters of cell culture media.

11. The adherent cell culture bioreactor of claim 9, wherein the substrate comprises at least about 60 m$^2$ of surface area for adherent cell culture.

12. The adherent cell culture bioreactor of claim 11, wherein the substrate comprises at least about 400 m$^2$ of surface area for adherent cell culture.

13. The adherent cell bioreactor of claim 9, wherein the feed-in pump and the feed-out pump are configured to provide a constant-rate output of cell culture medium at a pump output volume sufficient to maintain in said cell culture medium a concentration of lactate in said medium of not more than about 1.58 grams/liter.

14. The adherent cell bioreactor of claim 9, wherein the feed-in pump and the feed-out pump are configured to provide a constant-rate output of cell culture medium at a pump output volume sufficient to maintain in said cell culture medium a concentration of glucose in said medium of between about 0.5 and 1.0 grams/liter.

15. The adherent cell bioreactor of claim 9, wherein the feed-in pump and the feed-out pump are configured to provide a constant-rate output of cell culture medium at a pump output volume sufficient to maintain in said cell culture medium a concentration of glucose in said medium of not less than about 2.89 grams/liter.

16. A method for culturing adherent cells on a substrate comprising:
  a. obtaining the bioreactor of claim 9, and then
  b. adding to the bioreactor cell culture media and cells, and then
  c. culturing the cells in adherent mode on the substrate, while circulating the cell culture media about the cells at a rate to maintain in said cell culture medium a parameter selected from the group consisting of: concentration of lactate in said medium of not more than about 1.58 grams/liter; concentration of glucose in said medium of between about 0 .5 and 1.0 grams/liter; and concentration of glucose in said medium of not less than about 2.89 grams/liter.

17. The method of claim 16, the substrate providing at least about 60 m$^2$ of surface area for adherent cell culture.

18. The method of claim 17, the substrate providing at least about 400 m$^2$ of surface area for adherent cell culture.

19. The method of claim 16, the bioreactor configured to contain at least about 20 liters of cell culture media.

20. An adherent cell culture bioreactor comprising a substrate for adherent cell growth, a feed-in pump and a feed-out pump, wherein the feed-in pump and the feed-out pump are configured to provide a constant-rate output of media at an output volume of less than about 50 mL media per m$^2$ substrate area per day.

21. The adherent cell culture bioreactor of claim 20, wherein the bioreactor provides a volume of at least about 20 liters of cell culture media.

22. The adherent cell culture bioreactor of claim 20, wherein the substrate comprises at least about 60 m$^2$ of surface area for adherent cell culture.

23. The adherent cell culture bioreactor of claim 22, wherein the substrate comprises at least about 400 m$^2$ of surface area for adherent cell culture.

24. The adherent cell culture bioreactor of claim 20, wherein the feed-out pump is connected to the bioreactor via a tube having an interior diameter sized to accommodate the pump output volume of fluid without the formation of air bubbles inside the tube.

25. A method for culturing adherent cells on a substrate comprising:
  a. obtaining the bioreactor of claim 20, and then
  b. adding to the bioreactor cell culture media and cells, and then
  c. culturing the cells in adherent mode on the substrate, while circulating the cell culture media about the cells at a rate of less than about 50 mL of media per m$^2$ substrate area per day.

26. The method of claim 25, wherein the substrate comprises at least about 60 m$^2$ of surface area for adherent cell culture.

27. The method of claim 26, wherein the substrate comprises at least about 400 m$^2$ of surface area for adherent cell culture.

28. The method of claim 25, wherein the bioreactor provides a volume of at least about 20 liters of cell culture media.

29. An adherent cell culture bioreactor comprising a substrate for adherent cell growth, a feed-in pump and a feed-out pump, wherein the feed-in pump and the feed-out pump are configured to provide a constant-rate output of cell culture media sufficient to exchange the cell culture media in the vessel less than once every about 3½ days.

30. The adherent cell culture bioreactor of claim 29, wherein the feed-in pump and feed-out pumps are configured to provide a constant-rate output of cell culture media sufficient to exchange the cell culture media in the bioreactor at most once every about 4½ days.

31. The adherent cell culture bioreactor of claim 29, wherein the substrate comprises at least about 60 m$^2$ of surface area for adherent cell culture.

32. The adherent cell culture bioreactor of claim 31, wherein the substrate comprises at least about 400 m$^2$ of surface area for adherent cell culture.

33. The adherent cell culture bioreactor of claim 29, wherein the bioreactor provides a volume of at least about 20 liters of cell culture media.

34. A method for culturing adherent cells on a substrate comprising:
  a. obtaining the bioreactor of claim 29, and then
  b. adding to the bioreactor cell culture media and cells, and then
  c. culturing the cells in adherent mode on the substrate, while circulating the cell culture media about the cells at a rate of less than about 50 mL of media per 1,800 cells per day.

35. The method of claim 34, wherein the substrate comprises at least about 400 m$^2$ of surface area for adherent cell culture.

36. The method of claim 34, wherein the bioreactor provides a volume of at least about 20 liters of cell culture media.

37. The adherent cell culture bioreactor of claim 1, wherein the substrate for adherent cell culture comprises medical grade polyester microfibers.

* * * * *